(12) United States Patent
Slater et al.

(10) Patent No.: US 11,674,945 B2
(45) Date of Patent: Jun. 13, 2023

(54) SYSTEM AND METHOD FOR MEASURING PROPERTIES OF A FLUID

(71) Applicant: M-I L.L.C., Houston, TX (US)

(72) Inventors: Kenneth Slater, Sealy, TX (US); Bruno Lecerf, Houston, TX (US); Steven Philip Young, Cypress, TX (US); Chemsseddine Bouguetta, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 202 days.

(21) Appl. No.: 17/114,556

(22) Filed: Dec. 8, 2020

(65) Prior Publication Data
US 2022/0178906 A1 Jun. 9, 2022

(51) Int. Cl.
*G01N 33/28* (2006.01)
*B25J 11/00* (2006.01)

(52) U.S. Cl.
CPC ..... *G01N 33/2823* (2013.01); *G01N 33/2835* (2013.01); *B25J 11/005* (2013.01)

(58) Field of Classification Search
CPC .............. G01N 33/2823; G01N 33/2835
See application file for complete search history.

(56) References Cited

U.S. PATENT DOCUMENTS

| 5,086,646 A | * | 2/1992 | Jamison | G01N 9/00 73/61.63 |
| 5,677,478 A | * | 10/1997 | Murphy, Jr. | F16K 17/162 137/68.23 |
| 7,845,212 B1 | * | 12/2010 | Bi | G01N 15/04 73/865.6 |
| 10,520,484 B2 | * | 12/2019 | Miller | G01N 33/2823 |
| 2007/0137285 A1 | * | 6/2007 | Jennings | G01F 22/00 73/149 |
| 2017/0328829 A1 | * | 11/2017 | Lukay | F16J 15/028 |

(Continued)

OTHER PUBLICATIONS

OFITE, Thermocup with Removable Stainless-Steel Cup, Part No. 130-38-30 Instruction Manual, OFI Testing Equipment, Inc., Houston, Texas, 2013, 2 pages.

(Continued)

*Primary Examiner* — David Z Huang
*Assistant Examiner* — Jean F Morello (57) ABSTRACT

A device includes a housing having a bore formed axially therethrough. The housing includes a stop that protrudes radially inward proximate to a lower end of the housing. The device also includes a lower piston positioned in the bore. The lower piston is configured to move axially within the bore in response to a pressure differential across the lower piston. The lower piston is prevented from passing out through the lower end of the housing by the stop. The lower piston has a lower piston hole formed therethrough. The device also includes an upper piston positioned in the bore. The upper piston is configured to move axially within the bore in response to a pressure differential across the upper piston. The upper piston has an upper piston hole formed therethrough. The device is configured to receive a fluid in the bore, between the upper and lower pistons.

19 Claims, 11 Drawing Sheets

(56) References Cited

U.S. PATENT DOCUMENTS

2022/0178905 A1    6/2022  Slater et al.

OTHER PUBLICATIONS

OFITE, Thermocup, Product Bouchure, OFI Testing Equipment, Inc., Houston, Texas, 2015, 1 page.
OFITE, Teflon Liner for Aging Cells, Part No. 175-60 Instruction Manual, OFI Testing Equipment, Inc., Houston, Texas, 2013, 6 pages.
OFITE, Teflon Liner for Aging Cells, Product Brochure, OFI Testing Equipment, Inc., Houston, Texas, 2015, 1 page.

* cited by examiner

SYSTEM AND METHOD FOR MEASURING PROPERTIES OF A FLUID

BACKGROUND

Drilling fluid (also referred to as drilling mud) is a fluid, or a mixture of a fluid (e.g., including chemicals such as surfactants, fluid loss reducers, viscosifiers, emulsifiers, etc.) and solid particles, that is used to drill a wellbore in a subterranean formation. Drilling fluid may be water, oil, or synthetic-based. Oil or synthetic-based fluids are oftentimes oil continuous-phase emulsions, although some water-continuous phase emulsion fluids exist. The drilling fluid is oftentimes tested before or after use in the wellbore. Prior to testing, the drilling fluid may be first "aged" at an increased temperature and pressure. After being aged, the rheology of a first portion of the drilling fluid is tested. A filtration test may be performed on a second portion of the drilling fluid. In addition, other tests (e.g., chemical analysis, density, sag, lubricity, etc.) may also be performed on other portions of the drilling fluid.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

A device is disclosed. The device includes a housing having a bore formed axially therethrough. The housing includes a stop that protrudes radially inward proximate to a lower end of the housing. The device also includes a lower piston positioned in the bore. The lower piston is configured to move axially within the bore in response to a pressure differential across the lower piston. The lower piston is prevented from passing out through the lower end of the housing by the stop. The lower piston has a lower piston hole formed therethrough. The device also includes an upper piston positioned in the bore. The upper piston is configured to move axially within the bore in response to a pressure differential across the upper piston. The upper piston has an upper piston hole formed therethrough. The device is configured to receive a fluid in the bore, between the upper and lower pistons.

A system for determining a profile of a first fluid is also disclosed. The system includes a device. The device includes a housing having a bore formed axially therethrough. A lower end of the housing includes a stop that protrudes radially inward. The bore extends through the stop. The device also includes a lower piston positioned in the bore. The lower piston is configured to move axially within the bore in response to a pressure differential across the lower piston. The lower piston is prevented from passing out through the lower end of the housing by the stop. The lower piston has a lower piston hole formed therethrough. The device also includes an upper piston positioned in the bore. The upper piston is configured to move axially within the bore in response to a pressure differential across the upper piston. The upper piston has an upper piston hole formed therethrough. The device is configured to receive the first fluid in the bore, between the upper and lower pistons. The system also includes a first vessel configured to receive the device therein. A temperature and a pressure of the first fluid in the device are configured to be increased while the device is positioned within the first vessel.

A method for determining a profile of a first fluid is also disclosed. The method includes aging the first fluid. Aging the first fluid includes introducing the first fluid into a device. Aging the first fluid also includes introducing the device, with the first fluid therein, into a first vessel. Aging the first fluid also includes heating the first fluid to a predetermined temperature within the first vessel. Aging the first fluid also includes pressurizing the first fluid to a predetermined pressure within the first vessel. The method also includes performing a first test on the first fluid after the first fluid is aged. The first test is performed on the first fluid while the first fluid is in the device.

BRIEF DESCRIPTION OF THE DRAWINGS

The present disclosure is best understood from the following detailed description when read with the accompanying Figures. It is emphasized that, in accordance with the standard practice in the industry, various features are not drawn to scale. In fact, the dimensions of the various features may be arbitrarily increased or reduced for clarity of discussion.

DETAILED DESCRIPTION

Illustrative examples of the subject matter claimed below will now be disclosed. In the interest of clarity, not all features of an actual implementation are described in this specification. It will be appreciated that in the development of any such actual implementation, numerous implementation-specific decisions may be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

Further, as used herein, the article "a" is intended to have its ordinary meaning in the patent arts, namely "one or more." Herein, the term "about" when applied to a value generally means within the tolerance range of the equipment used to produce the value, or in some examples, means plus or minus 10%, or plus or minus 5%, or plus or minus 1%, unless otherwise expressly specified. Further, herein the term "substantially" as used herein means a majority, or almost all, or all, or an amount with a range of about 51% to about 100%, for example. Moreover, examples herein are intended to be illustrative only and are presented for discussion purposes and not by way of limitation.

Figure 1:
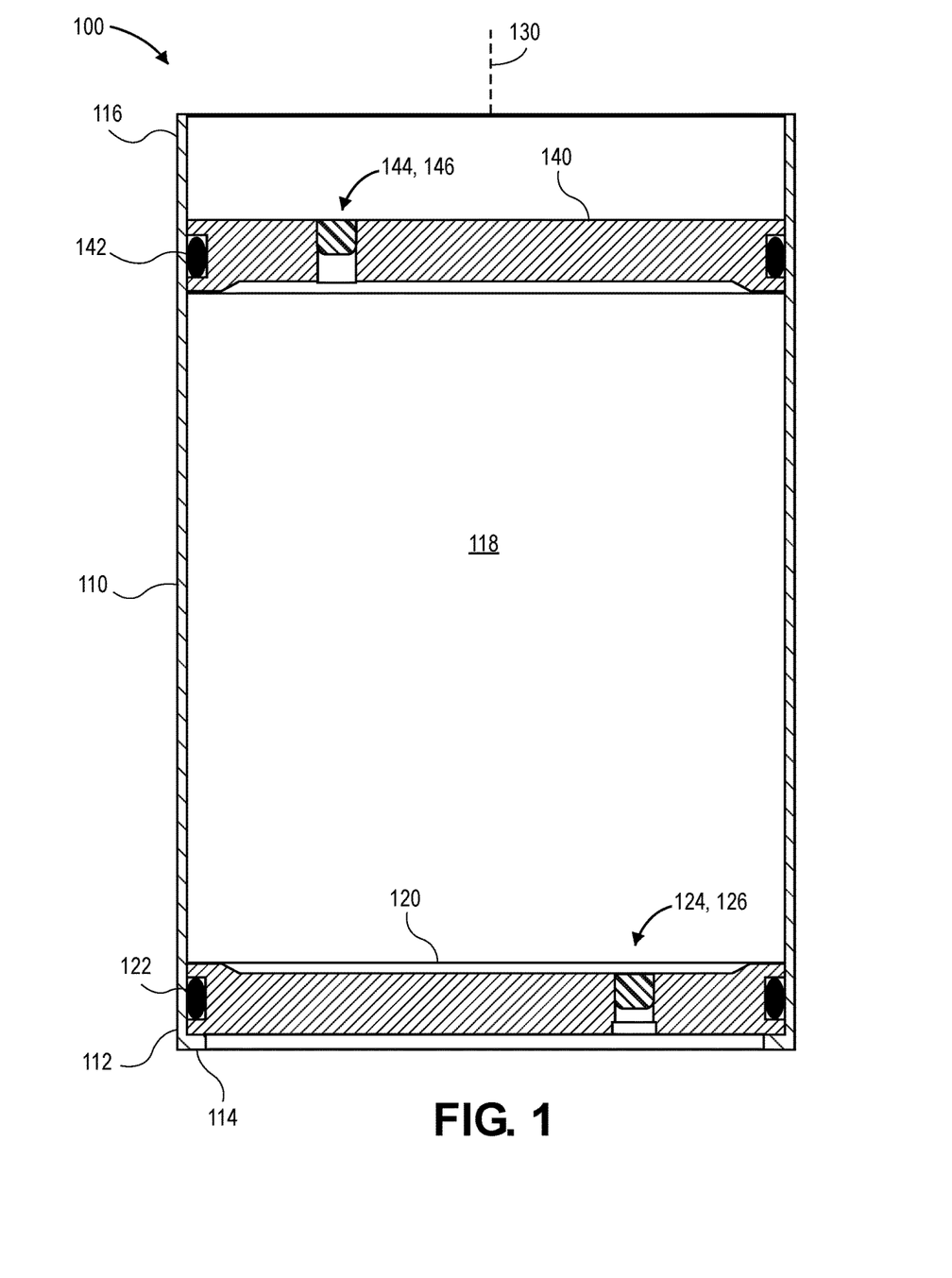
FIG. 1 illustrates a cross-sectional side view of a device for storing a fluid, according to an embodiment.

FIG. 1 illustrates a cross-sectional side view of a device (also referred to as a universal cup) 100 for storing a fluid, according to an embodiment. The fluid may be or include drilling fluid (also referred to as drilling mud). In one embodiment, the fluid may be collected from a wellbore. In another embodiment, the fluid may be prepared/mixed by a person (e.g., in a lab).

The device 100 may include a housing 110. The housing 110 may be substantially cylindrical; however, other shapes are also possible. A wall of the housing 110 may have a thickness from about 0.5 mm to about 5 mm or about 1 mm to about 3 mm. The housing 110 may be made from a metal, a polymer, a ceramic material, or a combination thereof. The housing 110 may have a first (e.g., lower) end 112 and a second (e.g., upper) end 116. The lower end 112 may include a stop 114 that protrudes inward from the housing 110. For example, the stop 114 may protrude radially inward from the wall of the housing 110 from about 1 mm to about 5 mm or about 1 mm to about 2 mm. Thus, the lower end 112 may define an opening therethrough. In another embodiment, instead of, or in addition to, the stop 114, the lower end 112 may be configured to have a lower cap coupled (e.g., threaded) thereto. The housing 110 may also have a bore 118 formed axially therethrough. The bore 118 may also be referred to as an inner volume.

The device 100 may also include a first (e.g., lower) piston 120 that is configured to be positioned at least partially within the housing 110. As shown, the lower piston 120 may be configured to land upon the stop 114. The lower piston 120 may be configured to move upward away from the stop 114 in response to a pressure differential across the lower piston 120, but the stop 114 may prevent the lower piston 120 from moving downward and exiting the housing 110 through the lower end 112. One or more seals (one is shown: 122) may be positioned at least partially between the housing 110 and the lower piston 120 to form a fluid-tight seal between the housing 110 and the lower piston 120. The seal 122 may be or include an O-ring.

The lower piston 120 may have one or more holes (one is shown: 124) formed therethrough. The hole 124 may extend from an upper surface to a lower surface of the lower piston 120. The lower piston 120 may also include a plug (also referred to as a "bleed plug") 126 that is configured to be positioned at least partially within the hole 124. The plug 126 is configured to prevent fluid from flowing through the hole 124. The plug 126 may have threads on an outer surface thereof that are configured to engage with threads on an inner surface of the lower piston 120 that defines the hole 124. In one embodiment, the hole 124 and the plug 126 may be substantially aligned with a central longitudinal axis 130 through the device 100 (e.g., through the housing 110 and/or the lower piston 120). However, as shown, in another embodiment, the hole 124 may be positioned on a first side of the axis 130 (e.g., to the right of the axis 130 as shown in FIG. 1). The hole 124 may be radially offset from the axis 130, which may help prevent the lower piston 120 from turning/rotating when the plug 126 is being turned/rotated to tighten and/or loosen the plug 126. The hole 124 and the plug 126 may be used during the filtration process described below. For example, the hole 124 may serve as a bleed hole.

The device 100 may also include a second (e.g., upper) piston 140 that is configured to be positioned at least partially within the housing 110. One or more seals (one is shown: 142) may be positioned at least partially between the housing 110 and the upper piston 140 to form a fluid-tight seal between the housing 110 and the upper piston 140. The seal 142 may be or include an O-ring.

The upper piston 140 may have one or more holes (one is shown: 144) formed therethrough. The hole 144 may extend from an upper surface to a lower surface of the upper piston 140. The upper piston 140 may also include a plug (also referred to as a "bleed plug") 146 that is configured to be positioned at least partially within the hole 144. The plug 146 is configured to prevent fluid from flowing through the hole 144. The plug 146 may have threads on an outer surface thereof that are configured to engage with threads on an inner surface of the upper piston 140 that defines the hole 144. In one embodiment, the hole 144 and the plug 146 may be substantially aligned with the axis 130. However, as shown, in another embodiment, the hole 144 and the plug 146 may be positioned on a second side of the axis 130 (e.g., to the left of the axis 130 as shown in FIG. 1). For example, the holes 124, 144 may be circumferentially offset from one another around the axis 130 from about 90° to about 270° (e.g., about 180°). The hole 124 may be radially offset from the axis 130, which may help prevent the upper piston 140 from turning/rotating when the plug 146 is being turned/rotated to tighten and/or loosen the plug 146.

Figure 2A:
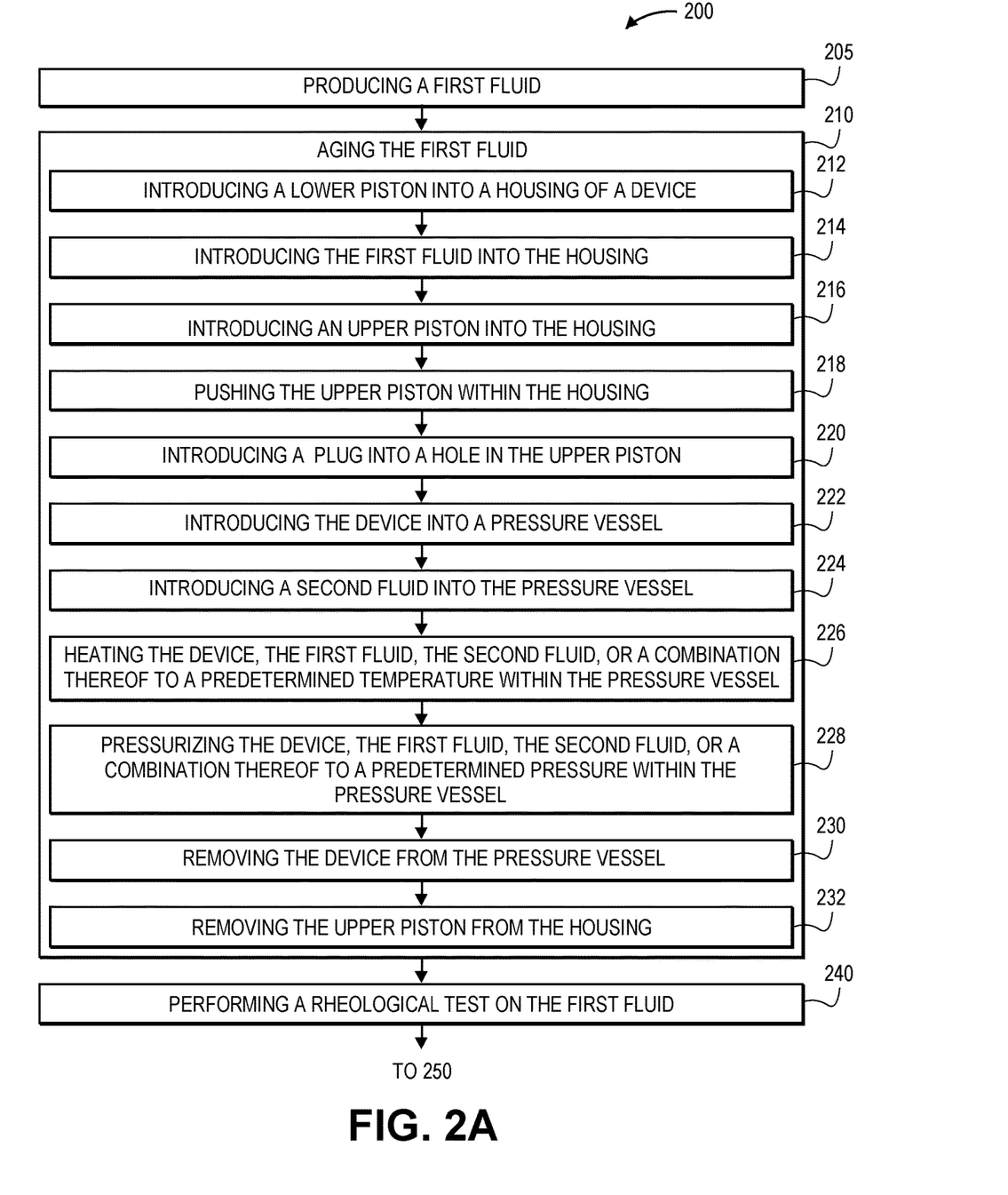
FIGS. 2A and 2B illustrate a flowchart of a method for performing a one or more tests on the fluid, according to an embodiment.
Figure 2B:
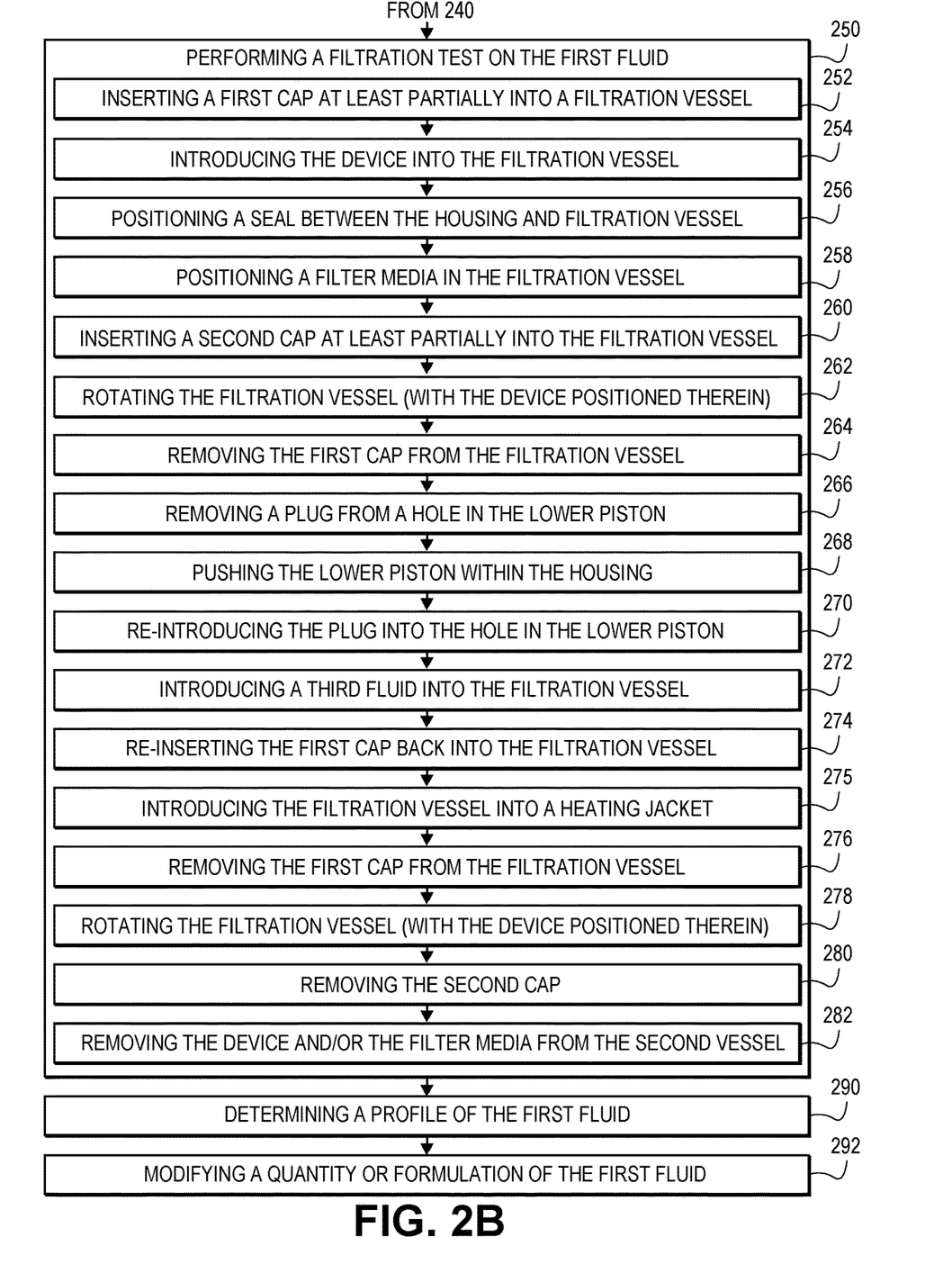

FIGS. 2A and 2B illustrate a flowchart of a method 200 for performing one or more tests on the fluid to determine a profile of the fluid, according to an embodiment. An illustrative order of the method 200 is provided below; however, one or more portions of the method 200 may be performed in a different order, performed simultaneously, repeated, or omitted. FIGS. 3-9 illustrate various portions of the method 200. In addition, one or more portions of the method 200 may be automated (e.g., using a robotic arm). This may increase the precision of the tests and decrease or prevent human exposure to the fluid being tested.

Referring, the method 200 may include producing a first fluid 150, as at 205. This may include mixing one or more ingredients together to produce the first fluid 150. For example, the ingredients may be mixed in the device 100 (e.g., the housing 110 and the lower piston 120). The ingredients may be or include chemicals such as surfactants, fluid loss reducers, viscosifiers, emulsifiers, etc.

Figure 3:
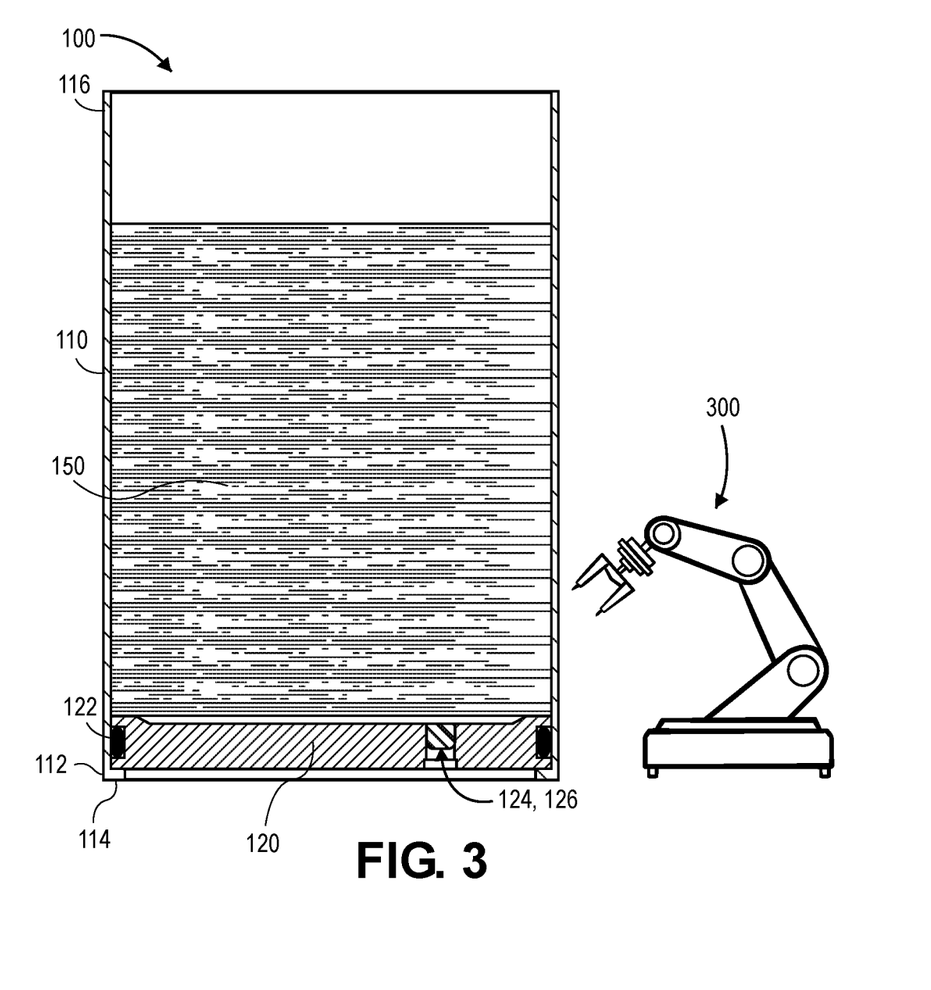
FIG. 3 illustrates a cross-sectional side view of a lower piston and a first fluid in the device, according to an embodiment.

The method 200 may also include aging the first fluid 150, as at 210. This is shown in FIG. 3. The first fluid 150 may be or include the drilling fluid (e.g., drilling mud) discussed above. The aging process may be or include a static aging process and/or a rolled aging process.

Aging the first fluid 150 may include introducing the lower piston 120 into the housing 110, as at 212. The lower piston 120 may be introduced into the housing 110 though the upper end 116 of the housing 110 using a robotic arm 300. The lower piston 120 may land on the stop 114. In one embodiment, the plug 126 may be positioned within the hole 124 when the lower piston 120 is introduced into the housing 110. The stop 114, the lower piston 120, the seal 122, the plug 126, or a combination thereof may prevent the first fluid 150 from leaking out of the lower end 112 of the housing 110. Thus, the housing 110 and the lower piston 120 may serve as a "cup."

Aging the first fluid 150 may also include introducing the first fluid 150 into the housing 110, as at 214. This is shown in FIG. 3. Introducing the first fluid 150 into the housing 110 may include pouring the first fluid 150 into the upper end 116 of the housing 110 using the robotic arm 300. The first fluid 150 may be within the inner volume 118 defined by the housing 110, the lower piston 120, or both. The first fluid 150 may fill from about 50% to about 90% or about 60% to about 80% of the inner volume 118.

Figure 4:
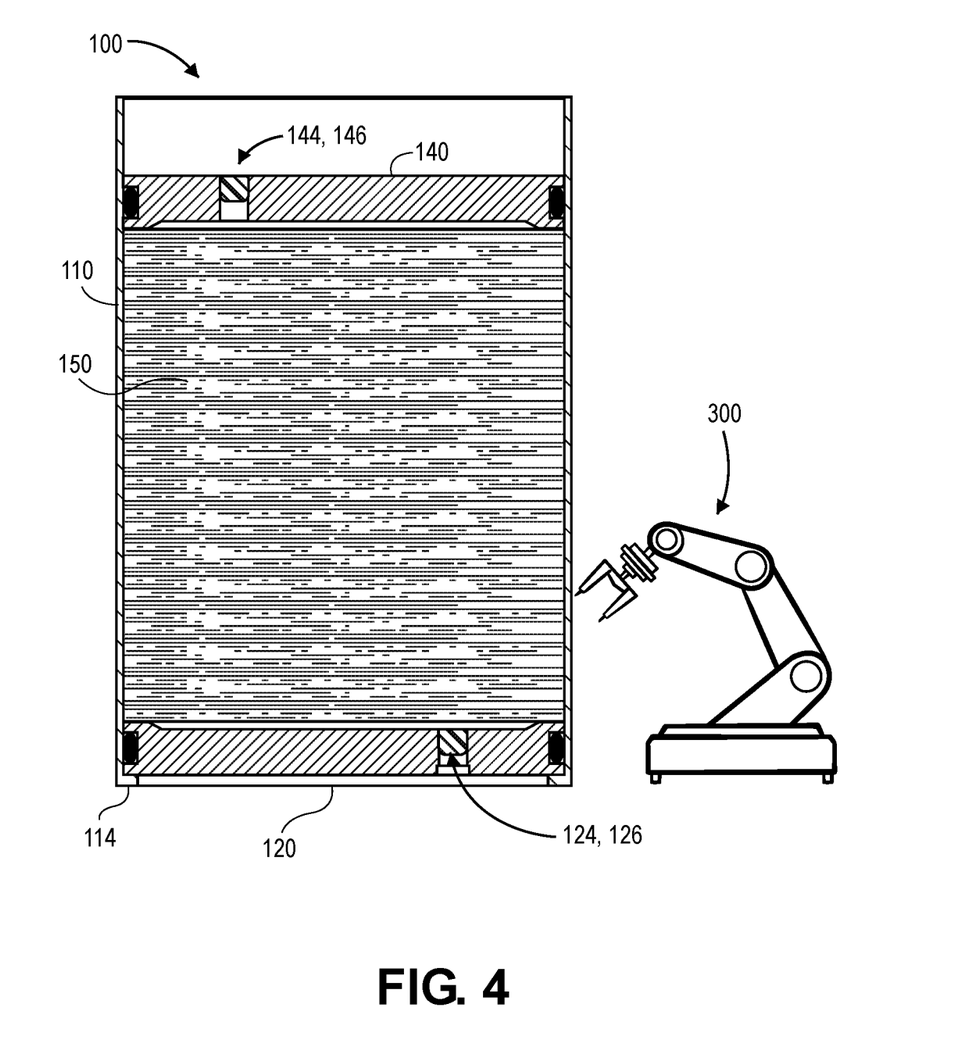
FIG. 4 illustrates a cross-sectional side view of an upper piston in the device, according to an embodiment.

Aging the first fluid 150 may also include introducing the upper piston 140 into the housing 110, as at 216. This is shown in FIG. 4. The upper piston 140 may be introduced through the upper end 116 of the housing 110 using the robotic arm 300. The upper piston 140 may be positioned at least partially above the first fluid 150. In at least one embodiment, the plug 146 may not be positioned within the hole 144 when the upper piston 140 is introduced into the housing 110.

Aging the first fluid 150 may also include pushing the upper piston 140 within the housing 110, as at 218. The upper piston 140 may be pushed downward toward the stop 114 using the robotic arm 300 until a portion of the first fluid 150 flows upward through the hole 144. Once the first fluid 150 flows through the hole 144, the user may conclude that there is no air left in the housing 110 below the upper piston 140, which may be beneficial for the following reasons. If air is trapped under the upper piston 140, the air may be dissolved into the first fluid 150 due to the pressure, temperature, and time in the vessel, as discussed below. When the device 100 is depressurized, the air may break-out and migrate in the device 100, which may disturb the upper layer of the first fluid 150 in the device 100. Any air trapped under the upper piston 140 may also or instead effervesce the first fluid 150 when the plug 146 is removed. In addition, any air trapped under the upper piston 140 may compress to near-zero volume, which may move the initial position of the upper piston 140 relative to the volumes of the samples taken. The portion of the first fluid 150 that flows through the hole 144 may be less than about 5%, less than about 3%, or less than about 1% of the first fluid 150 in the housing 110. The first fluid 150 that flows through the hole 144 may then be cleaned (e.g., vacuumed) out of the device 100.

Aging the first fluid 150 may also include introducing the plug 146 at least partially into the hole 144, as at 220. This is also shown in FIG. 4. Introducing the plug 146 at least partially into the hole 144 may include screwing the plug 146 into place within the upper piston 140 using the robotic arm 300. The plug 146 may then prevent the first fluid 150 from flowing through the hole 144.

Figure 5:
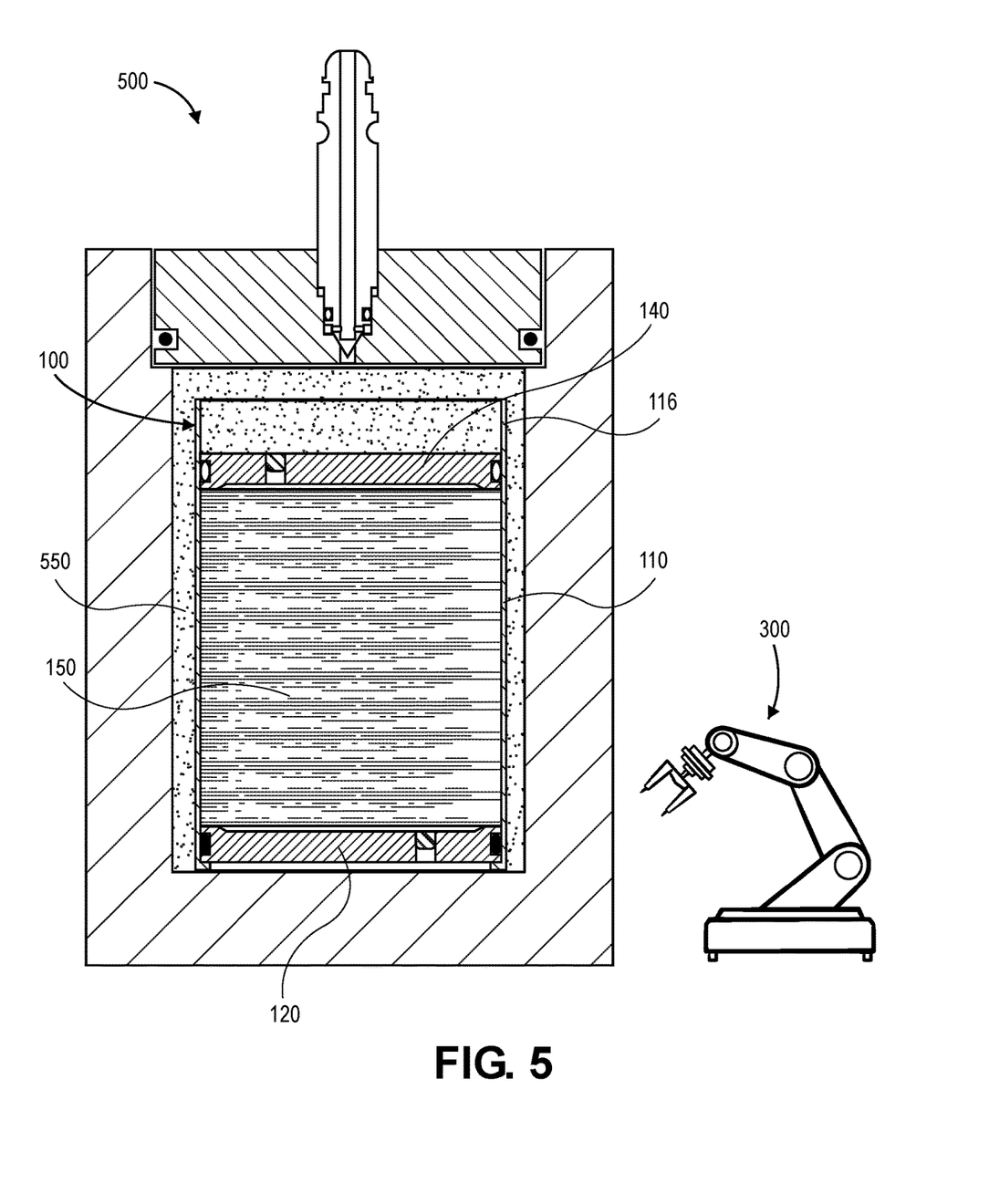
FIG. 5 illustrates a cross-sectional side view of the device in a pressure vessel, according to an embodiment.

Aging the first fluid 150 may also include introducing the device 100 into a first (e.g., pressure) vessel 500, as at 222. This is shown in FIG. 5. The device 100 may be inserted into the pressure vessel 500 using the robotic arm 300. Having the first fluid 150 contained within the device 100 may prevent the first fluid 150 from contacting and/or contaminating the inside of the pressure vessel 500. This may speed up the cleaning of the pressure vessel 500 as well as prevent corrosion inside the pressure vessel 500 that may be caused by the first fluid 150. In one embodiment, the pressure vessel 500 may be or include a consistometer. However, in other embodiments, the pressure vessel 500 may be or include any vessel that is configured to perform the one or more portions high temperature high pressure (HTHP) testing described below.

Aging the first fluid 150 may also include introducing a second fluid 550 into the pressure vessel 500, as at 224. This is also shown in FIG. 5. The second fluid 550 may be introduced into the pressure vessel 500 using the robotic arm 300. The second fluid 550 may be or include a hydraulic fluid. For example, the second fluid 550 may be or include water, oil, glycols, or a combination thereof. The second fluid 550 may at least partially surround the device 100 within the pressure vessel 500. In other words, the device 100 may be suspended or at least partially submerged within the second fluid 550. The second fluid 550 may flow at least partially into the device 100 (e.g., between the upper piston 140 and the upper end 116 of the housing 110). The upper piston 140 may provide a barrier between the first fluid 150 and the second fluid 550, which prevents the fluids 150, 550 from mixing. This may prevent the second fluid 550 from contaminating the first fluid 150, which may invalidate the test. The upper piston 140 may move axially within the housing 110 in response to a pressure differential between the first fluid 150 and the second fluid 550. In addition to the second fluid 550, a gas (e.g., nitrogen) may also be introduced into the pressure vessel 500. The nitrogen may help to pressurize the vessel 500, which may prevent vaporization of the first fluid 150.

Aging the first fluid 150 may also include heating the device 100, the first fluid 150, the second fluid 550, or a combination thereof to a predetermined temperature within the pressure vessel 500, as at 226. The predetermined temperature may be from about 150° C. to about 260° C. (500° F.) or about 175° C. to about 210° C.

Aging the first fluid 150 may also include pressurizing the device 100, the first fluid 150, the second fluid 550, or a combination thereof to a predetermined pressure within the pressure vessel 500, as at 228. The predetermined pressure may be from about 5 MPa to about 50 MPa or about 10 MPa to about 25 MPa (3,600 PSI).

The temperature and pressure may be coordinated (e.g., increased and/or decreased simultaneously). If the temperature is increased, the pressure will increase. The pressure is increased to the levels discussed above to realistically model the downhole environment. The device 100 may remain within the pressure vessel 500 at the high temperature and high pressure (HTHP) for a predetermined amount of time. The predetermined amount of time may be one or more days, weeks, or months. Maintaining the first fluid 150 at the HTHP for the predetermined duration may simulate wellbore conditions.

Aging the first fluid 150 may also include removing the device 100 from the pressure vessel 500, as at 230. The device 100 may be removed from the pressure vessel 500 using the robotic arm 300 after the predetermined amount of time when the device 100 and/or the first fluid 150 are back at the ambient temperature and pressure. Aging the first fluid 150 may also include removing the upper piston 140 from the housing 110, as at 232. The upper piston 140 may be removed using the robotic arm 300.

After the first fluid 150 is aged, the method 200 may also include performing one or more tests on the first fluid 150. In at least one embodiment, the first fluid 150 may remain within the device 100 during the one or more tests described below. In at least one embodiment, the one or more tests may be or include non-destructive tests (i.e., they may not damage or alter the first fluid 150).

The method 200 may include performing a rheological test on the first fluid 150, as at 240. The device 100 may be used for rheological testing in R1B1 configurations by using the housing 110 and lower piston 120 as a cup. For example, the device (e.g., the housing 110 and lower piston 120) may be introduced into a thermal conditioning block (also referred to as a thermal cup), which may be a temperature jacket that is configured to perform temperature testing between about 40° F. and about 150° F. The device (e.g., the housing 110 and lower piston 120) may be about the same size as a conventional cup so that it fits into the thermal conditioning block.

The method 200 may also or instead include performing a filtration test on the first fluid 150, as at 250. The filtration test may be performed before the rheological test, simultaneously with the rheological test, or after the rheological test. As described below, the filtration test may be performed on the first fluid 150 while the first fluid 150 is in the device 100.

Figure 6:
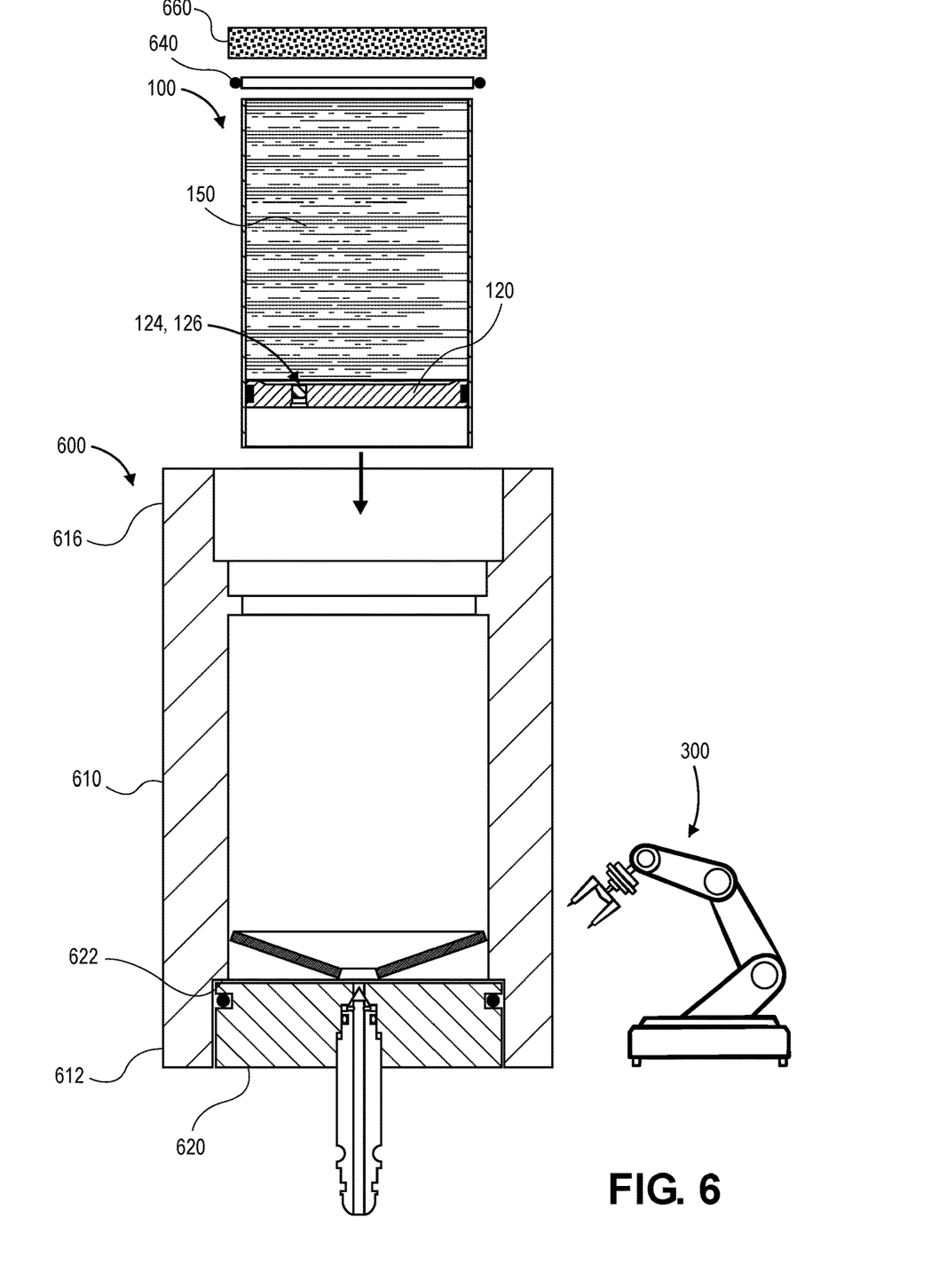
FIG. 6 illustrates a cross-sectional side view of the device being inserted into a filtration vessel, according to an embodiment.

Performing the filtration test may include inserting a first cap at least partially into a second (e.g., filtration) vessel 600, as at 252. This is shown in FIG. 6. The first cap may be inserted into the filtration vessel 600 using the robotic arm 300. The filtration vessel 600 may also be referred to as a filtration cell. The filtration vessel 600 may include a housing 610 having a first end 612 and a second end 616. The first cap 620 may be positioned at least partially within the housing 610 and proximate to the first end 612. The first cap 620 may contact a first shoulder 622 within the housing 610 that limits the upward axial movement of the first cap 620.

Figure 7:
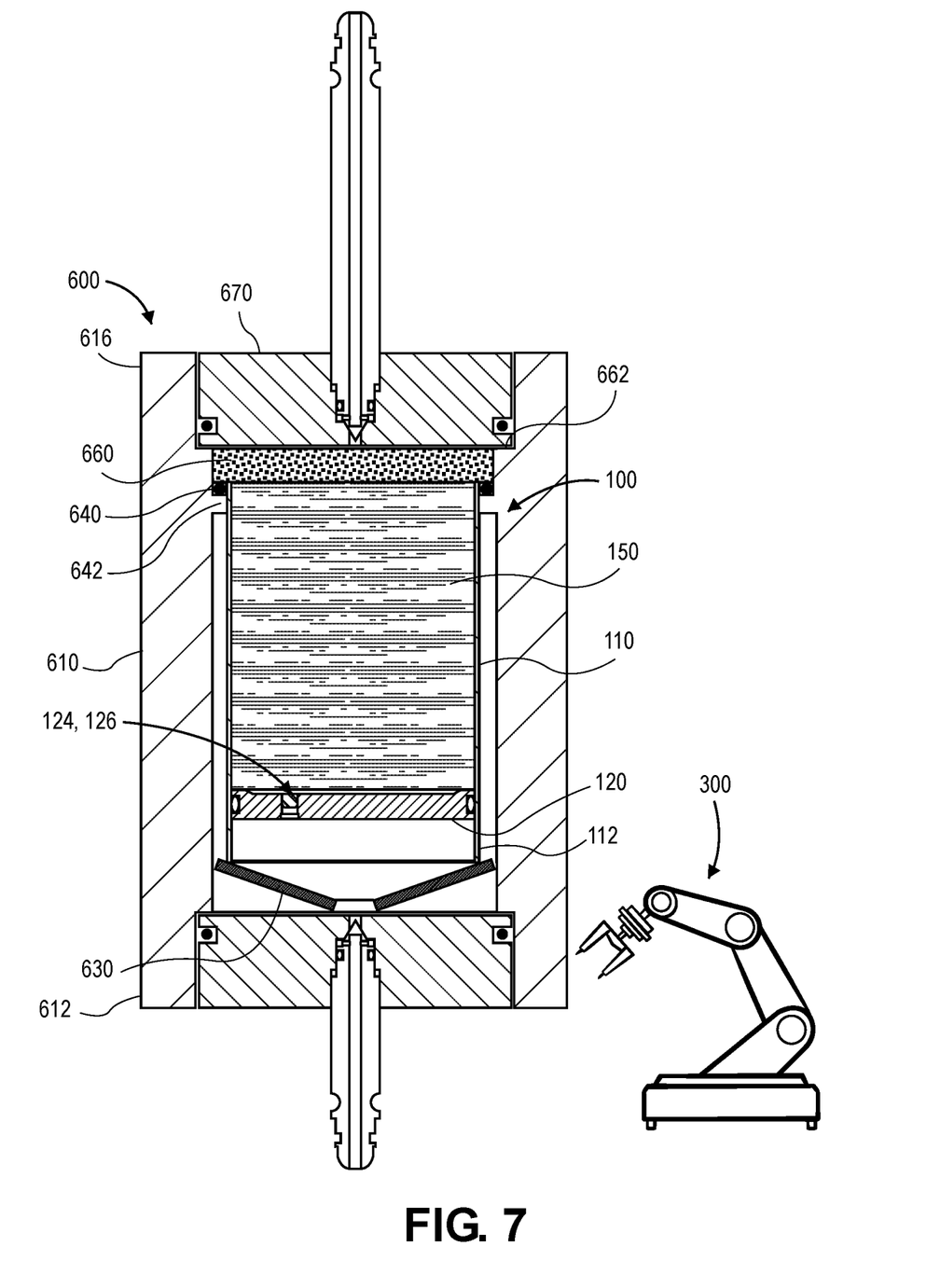
FIG. 7 illustrates a cross-sectional side view of the device positioned within the filtration vessel and secured between first and second caps of the filtration vessel, according to an embodiment.

Performing the filtration test may also include introducing the device 100 into the filtration vessel 600, as at 254. This is shown in FIGS. 6 and 7. Having the first fluid 150 contained within the device 100 may prevent the first fluid 150 from contacting and/or contaminating the inside of the filtration vessel 600. This may speed up the cleaning of the filtration vessel 600 as well as prevent corrosion inside the filtration vessel 600 that may be caused by the first fluid 150. The device 100 may be inserted using the robotic arm 300 with the lower end 112 and/or the lower piston 120 facing downward such that the first fluid 150 does not spill out of the housing 110. The lower end 112 and/or the lower piston 120 may be positioned proximate to the first cap 620. In one embodiment, one or more springs (one is shown: 630) may be positioned between the lower end 112 of the housing 110 and the first cap 620. The spring 630 may also or instead be positioned between the lower piston 120 and the first cap 620.

Performing the filtration test may also include positioning a seal 640 (e.g., radially) between the housing 110 of the device 100 and the housing 610 of the filtration vessel 600, as at 256. This is also shown in FIGS. 6 and 7. The seal 640 may be positioned using the robotic arm 300. The seal 640 may be or include an O-ring. The seal 640 may be positioned on a protrusion 642 that extends radially inward from the housing 610.

Performing the filtration test may also include positioning a filter media 660 in the filtration vessel 600, as at 258. This is also shown in FIGS. 6 and 7. The filter media 660 may be positioned on/over the upper end 116 of the housing 110 using the robotic arm 300 such that the first fluid 150 cannot flow out of the device 100 unless the first fluid 150 flows through the filter media 660. As shown, the seal 640 may be positioned axially between the shoulder 642 and the filter media 660.

Performing the filtration test may also include inserting a second cap 670 at least partially into the filtration vessel 600, as at 260. This is shown in FIG. 7. The second cap 670 may be positioned at least partially within the housing 610 (e.g., proximate to the second end 616) using the robotic arm 300. The second cap 670 may contact a second shoulder 662 within the housing 610 that limits downward axial movement of the second cap 670. The second cap 670 may also or instead contact the upper surface of the filter media 660. As shown, the device 100 may now be positioned between the first and second caps 620, 670. The spring 630 may at least partially compress to help hold the device 100 in place within the filtration vessel 600 and to compensate for temperature and/or pressure induced dimensional changes.

Figure 8:
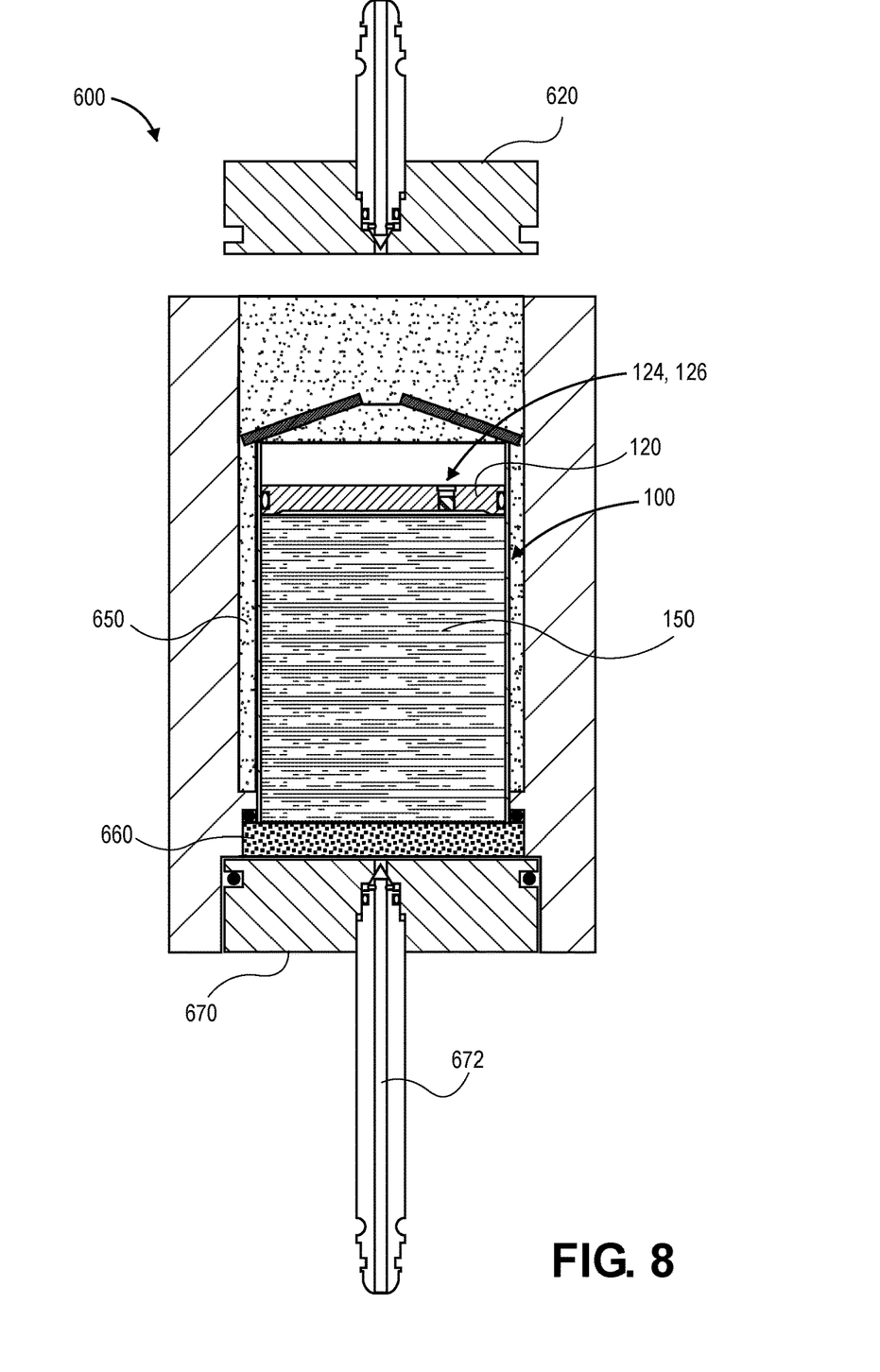
FIG. 8 illustrates a cross-sectional side view of the device and the filtration vessel flipped upside-down to perform a filtration test, according to an embodiment.

Performing the filtration test may also include rotating the filtration vessel 600 (with the device 100 positioned therein), as at 262. This is shown in FIG. 8. The filtration vessel 600 may be rotated using the robotic arm 300. This may include rotating the filtration vessel 600 by 180° (e.g., flipping the vessel 600 upside-down) such that the filter media 660 is now positioned below the device 100 and the first fluid 150.

Performing the filtration test may also include removing the first cap 620, as at 264. This is also shown in FIG. 8. This may be done using the robotic arm 300. Performing the filtration test may also include removing the plug 126 from the hole 124 in the lower piston 120, as at 266. This may be done using the robotic arm 300. Performing the filtration test may also include pushing the lower piston 120 within the housing 110, as at 268. This may be done using the robotic arm 300. For example, this may include pushing the lower piston 120 downward toward the filter media 660. This may cause any gas (e.g., air) within the device 100 to flow up and out of the device 100 through the hole 124. A nominal amount of the first fluid 150 may also flow up and out of the device 100 through the hole 124, which may indicate that the gas has been evacuated. Performing the filtration test may also include re-introducing the plug 126 into the hole 124 in the lower piston 120, as at 270. This may be done using the robotic arm 300. This may prevent fluid flow through the hole 124.

Performing the filtration test may also include introducing a third fluid 650 into the filtration vessel 600, as at 272. This is also shown in FIG. 8. The third fluid 650 may be poured into the filtration vessel 600 using the robotic arm 300. The third fluid 650 may be in the annulus between the device 100 and the filtration vessel 600. The third fluid 650 may at least partially surround the device 100. In one embodiment, a portion of the third fluid 650 may flow into the device 100. In the example shown, the third fluid 650 may flow into the housing 110 between the lower piston 120 and the lower end 112 of the housing 110. The lower piston 120 and the plug 126 may prevent the first and third fluids 150, 650 from mixing. The third fluid 650 may serve as a heat transfer medium between the device 100 and the filtration vessel 600. The third fluid 650 may be or include water, oil, glycols, or a combination thereof.

Figure 9:
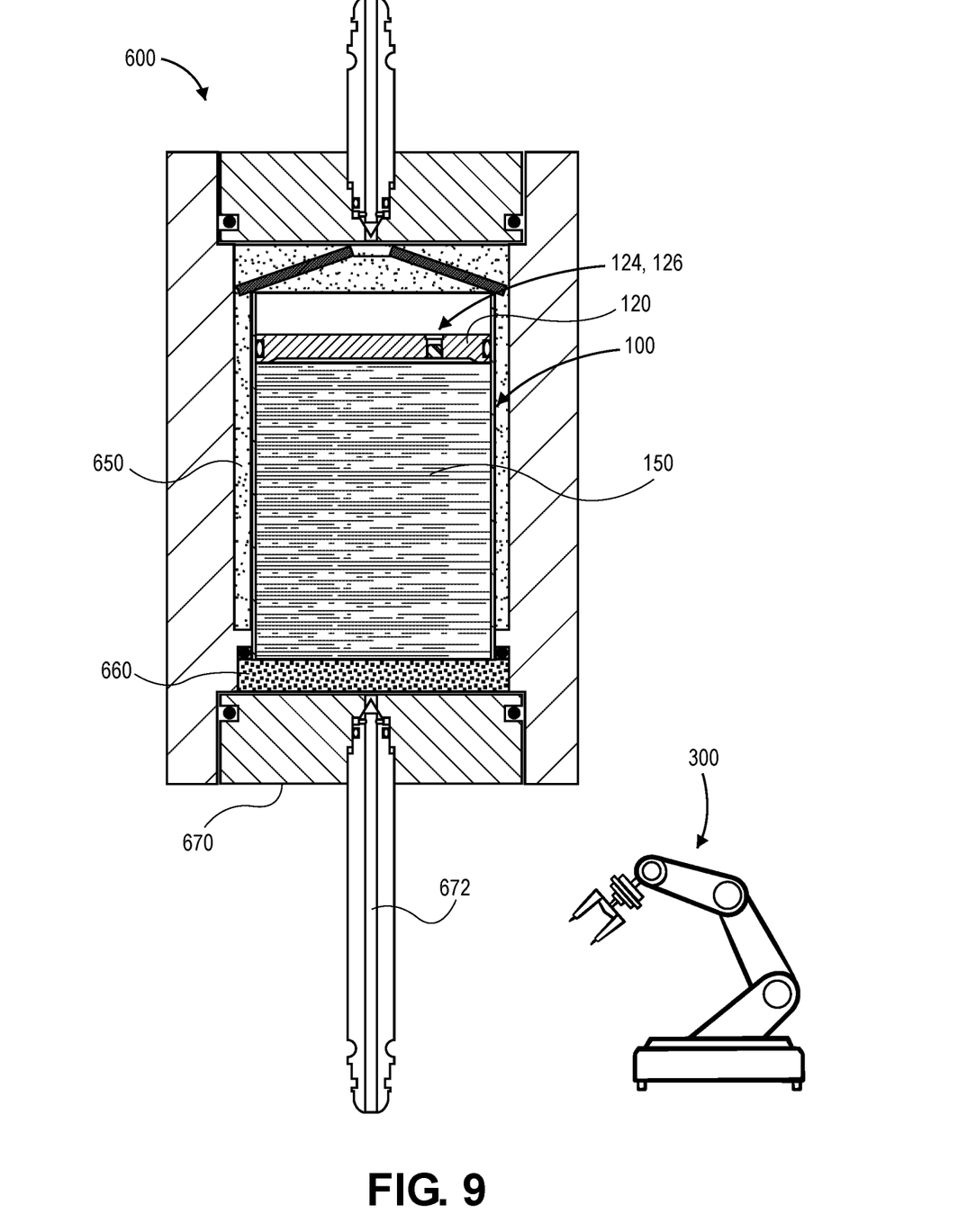
FIG. 9 illustrates a cross-sectional side view of the device and the filtration vessel after a plug is removed from the device and a second fluid is added into the filtration vessel, according to an embodiment.

Performing the filtration test may also include re-inserting the first cap 620 back into the filtration vessel 600, as at 274. This is shown in FIG. 9. This may be done using the robotic arm 300. Performing the filtration test may also include introducing the filtration vessel 600 into a heating jacket, as at 275. In one embodiment, pressurization for the filtration process may be hydraulic. In another embodiment, pressurization for the filtration process may use a gas (e.g., nitrogen) pressure supply.

A portion of the first fluid 150 may flow through the filter media 660. The portion of the first fluid 150 may then flow through a bore 672 in the second cap 670. This portion of the first fluid 150 is referred to as filtrate. The quantity of filtrate over a predetermined period of time may be determined. In addition, the chemical properties of the filtrate may then be tested. For example, water-based mud may be tested for alkalinities, chlorides, hardness (e.g., ions in the fluid). In another example, oil-based mud may be tested for water and/or alkalinities.

Figure 10:
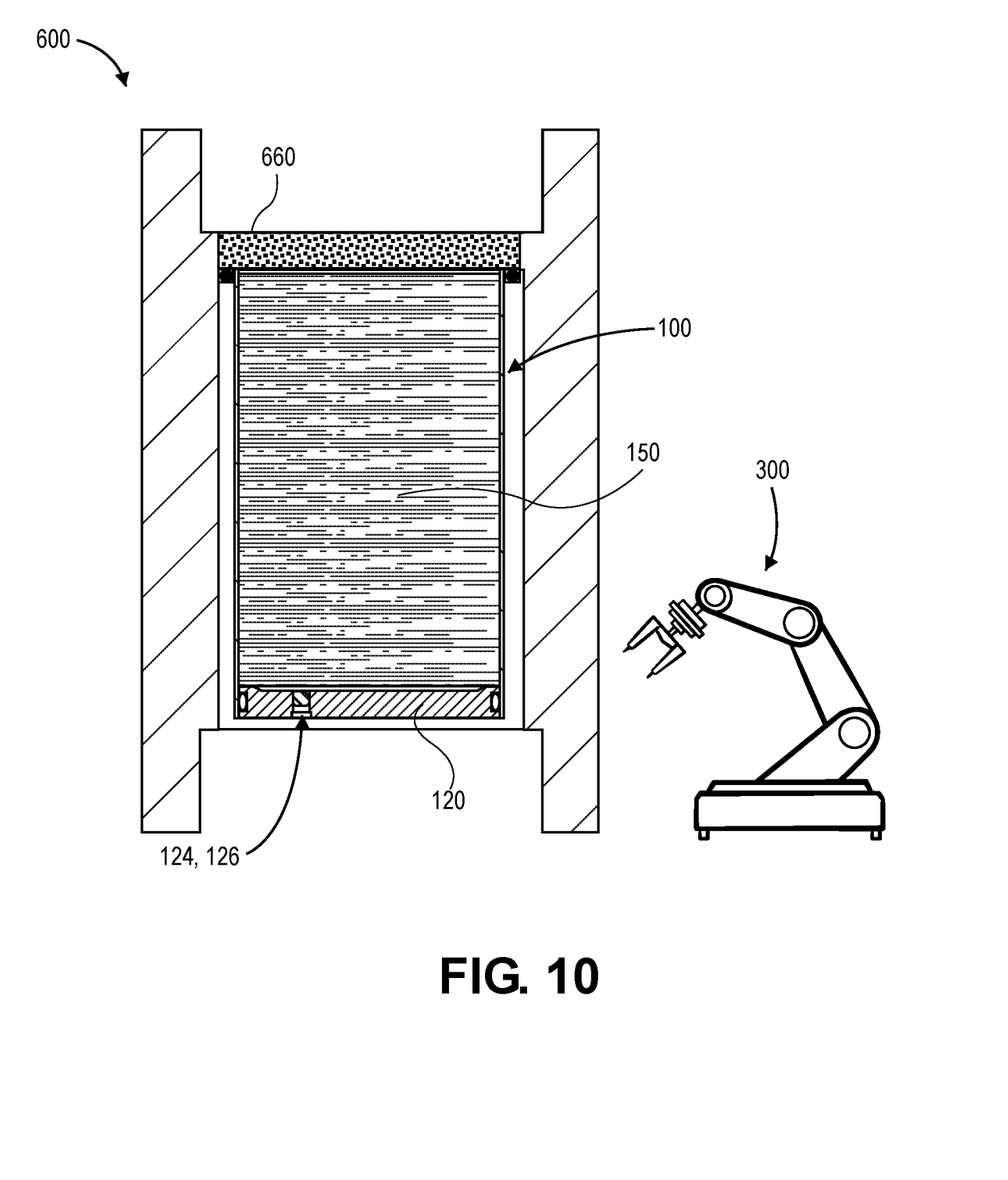
FIG. 10 illustrates a cross-sectional side view of the device and the filtration vessel flipped right-side-up after the filtration test, according to an embodiment.

Performing the filtration test may also include removing the first cap 620 and/or the spring 630 from the filtration vessel 600, as at 276. This is shown in FIG. 10. This may be done using the robotic arm 300. Performing the filtration test may also include rotating the filtration vessel 600 (with the device 100 positioned therein), as at 278. This is also shown in FIG. 10. This may include rotating filtration vessel 600 by 180° (e.g., flipping the vessel 600 right side-up) using the robotic arm 300 such that the filter media 660 is now positioned above the device 100 and the first fluid 150. The third fluid 650 may flow out of (or be removed from) the second vessel 600. Performing the filtration test may also include removing the second cap 670, as at 280. This is also shown in FIG. 10. The second cap 670 may be removed using the robotic arm 300. Performing the filtration test may also include removing the device 100 and/or the filter media 660 from the second vessel 600, as at 282. The filter media 660 and/or filter cakes may be analyzed to determine their thickness and/or toughness.

The method 200 may also include determining a profile (also referred to as a characterization) of the first fluid 150, as at 290. As used herein, the "profile" refers to physical and/or chemical properties of the first fluid 150. The profile may also include a performance in comparison to predetermined parameters. The profile may be determined based at least partially upon the rheological test, the filtration test, or both. If the profile is outside of a predetermined threshold, the method 200 may also include modifying a quantity or formulation of the first fluid 150, as at 292. Once the quantity and/or formulation of the first fluid 150 has been modified, the method 200 may loop back to 214 to test the new quantity/formulation.

As discussed above, the first fluid 150 may be stored within the device 100 while the first fluid 150 is prepared/mixed, while the first fluid 150 is aged, while a rheology test is performed on the first fluid 150, while a filtration test is performed on the first fluid 150, while one or more other tests (e.g., shear test, sag test, density test, etc.) are performed on the first fluid 150, or a combination thereof. In addition, storing the first fluid 150 within the device 100 during the aging and/or filtration tests may prevent the first fluid 150 from contacting or corroding the vessels 500, 600. The robotic arm 300 may remove human error from the process and may also increase safety by reducing human exposure to the first fluid 150.

Thus, the present disclosure may provide an electromechanical system with inputs of fluid recipes and ingredients (also referred to as products) that may mix a sample in the device (i.e., the universal cup) 100, age the sample, measure fluid rheology, determine filtration characteristics, determine density, perform solids analysis etc. This may be done with no human intervention other than loading the equipment and interpreting the analyzed test data. The device 100 may be used to handle fluids robotically in the above-mentioned system.

In addition, the method 200 may be used to automate the formulation and evaluation of fluid samples. Multiple formulations can be automatically mixed and evaluated to determine individual product performance, optimum concentration, effect on one or more mud properties including rheology, fluid loss etc. Thus, instead of a person manually mixing and testing multiple formulation variations, the device 100 may enable automated machinery to perform this function by providing a single universal fluid sample holder that is amenable to robotic manipulation through the various mixing, and sample evaluation to be performed.

In at least one embodiment, the device 100, the robotic arm 300, the first (e.g., pressure) vessel 500, the second (e.g., filtration) vessel 600, or a combination thereof may be positioned on/in a vehicle (e.g., on the back of a truck). This may allow a user (e.g., a mud engineer) to drive the truck to a plurality of different rig locations and perform at least a portion of the method 200 at each rig location. As will be appreciated, this may save time, increase the number of rigs that the user may visit in a day, and/or reduce the number of users that are visiting the rigs.

For example, upon arrival at a rig location, the mud engineer may count inventory to consolidate with a derrick hand's list of chemicals. The mud engineer may also walk to the pits to observe the circulating system. The mud engineer may also walk to the drill floor and collect information from the drilling engineer. The mud engineer may also collect directional drilling information before running a full mud check (e.g., using at least a portion of the method 200). The mud engineer may also collect drilling data for a DMR from the rig's geolograph. The mud engineer may also collect mud samples from the flow line, underneath the shakers, in the suction pits, in the solids control equipment, in the premixing tanks, in the reserve tank, or a combination thereof. The mud may then be tested (e.g., using at least a portion of the method 200).

As used herein, the terms "inner" and "outer"; "up" and "down"; "upper" and "lower"; "upward" and "downward"; "upstream" and "downstream"; "above" and "below"; "inward" and "outward"; and other like terms as used herein refer to relative positions to one another and are not intended to denote a particular direction or spatial orientation. The terms "couple," "coupled," "connect," "connection," "connected," "in connection with," and "connecting" refer to "in direct connection with" or "in connection with via one or more intermediate elements or members."

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific examples are presented for purposes of illustration and description. They are not intended to be exhaustive of or to limit this disclosure to the precise forms described. Many modifications and variations are possible in view of the above teachings. The examples are shown and described in order to best explain the principles of this disclosure and practical applications, to thereby enable others skilled in the art to best utilize this disclosure and various examples with various modifications as are suited to the particular use contemplated. It is intended that the scope of this disclosure be defined by the claims and their equivalents below.

What is claimed is:

1. A device, comprising:
   a housing having a bore formed axially therethrough, wherein the housing comprises a stop that protrudes radially inward proximate to a lower end of the housing;
   a lower piston positioned in the bore, wherein the lower piston is configured to move axially within the bore in response to a pressure differential across the lower piston, wherein the lower piston is prevented from passing out through the lower end of the housing by the stop, and wherein the lower piston has a lower piston hole formed therethrough; and an upper piston positioned in the bore, wherein the upper piston is configured to move axially within the bore in response to a pressure differential across the upper piston, wherein the upper piston has an upper piston hole formed therethrough, and wherein the device is configured to receive a fluid in the bore, between the upper and lower pistons.

2. The device of claim 1, wherein the bore extends through the stop.

3. The device of claim 2, wherein the lower piston, when in contact with the stop, prevents the fluid from flowing out of the lower end of the housing.

4. The device of claim 3, wherein the lower piston, when spaced apart from the stop, prevents the fluid from flowing out of the lower end of the housing.

5. The device of claim 4, further comprising:
a lower piston plug that is configured to be threaded into the lower piston hole to prevent the fluid from flowing through the lower piston hole; and
an upper piston plug that is configured to be threaded into the upper piston hole to prevent the fluid from flowing through the upper piston hole.

6. A system for determining a profile of a first fluid, comprising:
a device comprising:
a housing having a bore formed axially therethrough, wherein a lower end of the housing includes a stop that protrudes radially inward, and wherein the bore extends through the stop;
a lower piston positioned in the bore, wherein the lower piston is configured to move axially within the bore in response to a pressure differential across the lower piston, wherein the lower piston is prevented from passing out through the lower end of the housing by the stop, and wherein the lower piston has a lower piston hole formed therethrough; and
an upper piston positioned in the bore, wherein the upper piston is configured to move axially within the bore in response to a pressure differential across the upper piston, wherein the upper piston has an upper piston hole formed therethrough, and wherein the device is configured to receive the first fluid in the bore, between the upper and lower pistons; and
a first vessel configured to receive the device therein, wherein a temperature and a pressure of the first fluid in the device are configured to be increased while the device is positioned within the first vessel.

7. The system of claim 6, further comprising:
a lower piston plug that is configured to be threaded into the lower piston hole to prevent the first fluid, the second fluid, or both from flowing through the lower piston hole; and
an upper piston plug that is configured to be threaded into the upper piston hole to prevent the first fluid, the second fluid, or both from flowing through the upper piston hole.

8. The system of claim 6, wherein the first vessel is configured to receive a second fluid therein, and wherein the device is at least partially submerged within the second fluid.

9. The system of claim 8, wherein the bore is configured to have the second fluid flow therein, and wherein the lower piston, the upper piston, or both prevent the first and second fluids from mixing in the bore.

10. The system of claim 6, further comprising a second vessel, wherein the device is configured to be removed from the first vessel and subsequently introduced into the second vessel.

11. The system of claim 10, further comprising a robotic arm that is configured to introduce the device into the first vessel, remove the device from the first vessel, introduce the device into the second vessel, or a combination thereof.

12. The system of claim 10, further comprising a filter media that is configured to be positioned at least partially within the second vessel.

13. The system of claim 12, wherein the second vessel is configured to be inverted when the device and the filter media are positioned at least partially therein, causing a portion of the first fluid to flow through the filter media.

14. The system of claim 12, wherein the second vessel comprises:
a first cap positioned at least partially within a first end of the second vessel;
a spring positioned at least partially within the second vessel and between the first cap and the lower end of the housing; and
a second cap positioned at least partially within a second end of the second vessel, wherein the filter media is positioned between the second cap and the device.

15. The system of claim 12, wherein the second vessel comprises:
a shoulder that protrudes radially inward toward the device; and
a seal positioned on the shoulder, wherein the seal is positioned radially between the device and the second vessel and axially between the shoulder and the filter media.

16. A method for determining a profile of a first fluid, comprising:
aging the first fluid, wherein aging the first fluid comprises:
introducing the first fluid into a device; and
introducing the device, with the first fluid therein, into a first vessel;
heating the first fluid to a predetermined temperature within the first vessel; and
pressurizing the first fluid to a predetermined pressure within the first vessel; and
performing a first test on the first fluid after the first fluid is aged, wherein the first test is performed on the first fluid while the first fluid is in the device;
wherein aging the first fluid further comprises:
introducing a lower piston into a housing of the device using a robotic arm prior to introducing the first fluid into the housing of the device;
introducing an upper piston into the housing of the device using the robotic arm after introducing the first fluid into the housing of the device, wherein the first fluid is positioned at least partially between the lower and upper pistons;
pushing the upper piston downward using the robotic arm, which causes a portion of the first fluid to flow through a hole in the upper piston; and
introducing a plug into the hole using the robotic arm after the portion of the first fluid flows through the hole.

17. The method of claim 16, further comprising mixing two or more ingredients together in the device to produce the first fluid.

18. The method of claim 16, wherein performing the first test on the first fluid comprises:
introducing the device, with the first fluid therein, into a second vessel using a robotic arm;
introducing a filter media into the second vessel using the robotic arm; and rotating the second vessel using the robotic arm, with the device and the filter media therein, such that the filter media becomes positioned below the device, which causes at least a portion of the first fluid to flow through the filter media.

19. The method of claim 16, wherein the first test comprises a filtration test, and further comprising performing a rheological test on the first fluid after the first fluid is aged, wherein the rheological test is performed on the first fluid while the first fluid is in the device.

* * * * *